United States Patent [19]

Rogers et al.

[11] Patent Number: 4,474,599
[45] Date of Patent: Oct. 2, 1984

[54] 1-(PYRIDYL)-1H-1,2,3-TRIAZOLE DERIVATIVES, AND USE AS HERBICIDAL AGENTS

[75] Inventors: Richard B. Rogers; Ben C. Gerwick, both of Concord; Eric A. Egli, Walnut Creek, all of Calif.

[73] Assignee: The Dow Chemical Company, Midland, Mich.

[21] Appl. No.: 398,451

[22] Filed: Jul. 14, 1982

[51] Int. Cl.³ .................. A01N 43/40; A01N 43/64; C07D 401/04; C07D 405/14
[52] U.S. Cl. ..................... 71/92; 71/94; 424/263; 546/256; 546/276; 546/283
[58] Field of Search ............... 544/336, 198, 324, 238, 544/328, 331, 298, 207, 209, 212; 548/255; 546/276, 256, 283; 424/249, 250, 263, 269; 71/92, 93, 94

[56] References Cited

U.S. PATENT DOCUMENTS

| | | |
|---|---|---|
| 3,470,196 | 9/1969 | Harvey et al. |
| 3,754,001 | 8/1973 | Timmler et al. |
| 4,013,441 | 3/1977 | Bianchetti et al. ............... 548/255 |
| 4,166,854 | 9/1979 | Carson et al. |
| 4,212,869 | 7/1980 | Carson et al. |
| 4,215,127 | 7/1980 | Rogers et al. |

FOREIGN PATENT DOCUMENTS

| | | |
|---|---|---|
| 7003694 | 9/1970 | Netherlands. |
| 2070607 | 3/1981 | United Kingdom. |

OTHER PUBLICATIONS

Bianchetti et al., C.A. 82171b, 1967, vol. 67, p. 7749, col. II.
Banks et al. (I), C.A. 78-58205x and J.C.S. Perkin I 1, 1972, (23), pp. 2964-2970, (Eng).
Messmer et al., Index Chemicus, vol. 4, No. 1, 1/15/62.
Aufderhaar et al., C.A. 78815v, vol. 79, 1973, p. 502.
Hubert et al., C.A. 53669j, vol. 74, 1971, p. 355.
Huisgen et al., C.A. 812965, vol. 71, 1969, p. 399.
Banks et al., (II), C.A. 125237g, vol. 82, 1975, p. 547.

*Primary Examiner*—Henry R. Jiles
*Assistant Examiner*—J. G. Mullins
*Attorney, Agent, or Firm*—Ronald G. Brookens

[57] ABSTRACT

Compounds are prepared which correspond to the formula

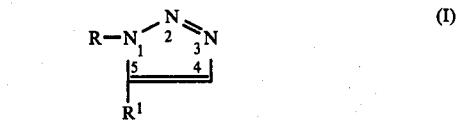

wherein
R represents $C_1$-$C_{12}$ alkyl, $C_1$-$C_{12}$ alkoxyalkyl, —$CH_2Ar$, $Ar'$;
Ar represents

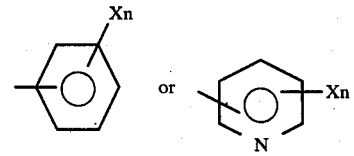

each X independently represents halo, $C_1$-$C_6$ alkyl, —$OCH_3$, —$CF_3$, —$OCF_3$, —$NO_2$, —$CN$ or —$CO_2R^2$;
each n independently represents 0, 1 or 2;
Ar' represents

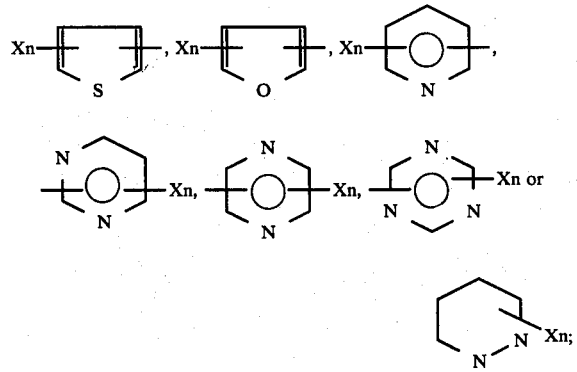

$R^1$ represents $C_1$-$C_8$ alkyl, $C_2$-$C_6$ alkenyl, $C_2$-$C_6$ alkynyl, $C_2$-$C_6$ alkoxyalkyl, $CF_3$ or $Ar''$;
Ar'' represents Ar,

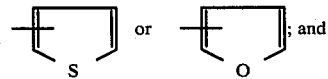

$R^2$ represents $C_1$-$C_6$ alkyl.

These compounds have been found to be effective pre- and post-emergent herbicides and as active agents in herbicidal compositions.

30 Claims, No Drawings

1-(PYRIDYL)-1H-1,2,3-TRIAZOLE DERIVATIVES, AND USE AS HERBICIDAL AGENTS

BACKGROUND OF INVENTION

The present invention relates to novel substituted-1,2,3-triazole compounds, to compositions containing said compounds, to the use of such compounds and compositions as herbicides and to novel intermediates used in the preparation of said compounds.

U.S. Pat. Nos. 4,013,441 and 3,470,196 both disclose 1-(substituted phenyl)-5-(substituted)-1,2,3-triazole compounds which possess herbicidal activity. U.K. patent application No. 2,070,607 discloses 1-(3,5-ditrifluoromethylphenyl)-5- phenyl-1,2,3-triazole derivatives useful as plant growth regulating agents.

SUMMARY OF INVENTION

The present invention is directed to novel substituted-1,2,3-triazoles of the following formula:

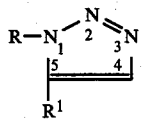
(I)

wherein

R represents $C_1$–$C_{12}$ alkyl, $C_1$–$C_{12}$ alkoxyalkyl, —$CH_2Ar$, Ar';

Ar represents

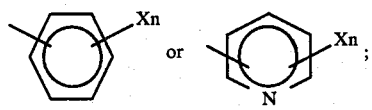

each X independently represents halo, $C_1$–$C_6$ alkyl, —$OCH_3$, —$CF_3$, —$OCF_3$, —$NO_2$, —$CN$, or —$CO_2R^2$;

each n independently represents 0, 1 or 2;

Ar' represents

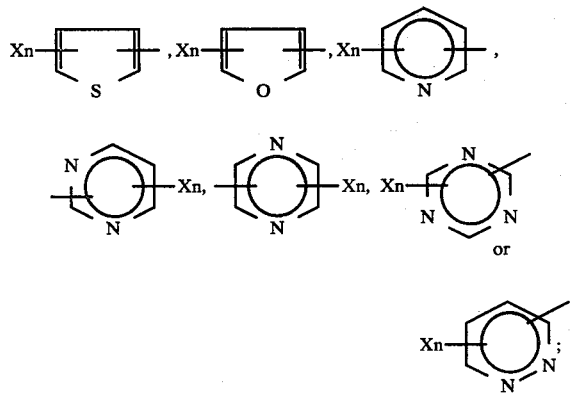

$R^1$ represents $C_1$–$C_8$ alkyl, $C_2$–$C_6$ alkenyl, $C_2$–$C_6$ alkynyl, $C_2$–$C_6$ alkoxyalkyl, $CF_3$ or Ar";

Ar" represents Ar,

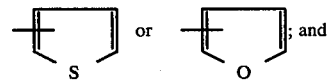

$R^2$ represents $C_1$–$C_6$ alkyl.

The compounds of the above Formula I, hereinafter referred to as "active ingredients", have been found to be active as herbicides. Accordingly, the present invention also encompasses compositions containing one or more active ingredients as well as methods of controlling unwanted vegetation. Such methods comprise applying a herbicidally effective amount of one or more active ingredients preemergently or post-emergently to the locus of the undesired vegetation, and particularly to the locus where a valuable crop is to germinate and grow.

DETAILED DESCRIPTION

The term "herbicide" is used herein to mean an active ingredient which controls or adversely modifies the growth of plants because of phytotoxic or other effects substantial enough to seriously retard the growth of the plant or further damage the plant sufficiently to kill it. By "growth controlling" or "herbicidally-effective" amount is meant an amount of active ingredient which causes a modifying effect and includes deviations from natural development, killing, regulation, dessication, retardation, and the like. The term "plants" is meant to germinant seeds, emerging seedlings and established vegetation.

The terms "$C_1$–$C_{12}$", "$C_1$–$C_8$", "$C_1$–$C_6$", and "$C_2$–$C_6$" are meant to indicate the number of carbon atoms that can be present in the group that the terms modify. The term "alkyl" is meant to encompass straight, branched or cycloalkyl groups when the group has 3 or more carbon atoms. The term "halo" is used herein to include chloro, fluoro, iodo and bromo.

The active ingredients of the present invention are generally crystalline solids at ambient temperatures which are soluble in many organic solvents commonly employed as herbicidal carriers such as, alcohols, acetone, xylenes and methylene chloride. The active ingredient of the above Formula I which is 2-(5-phenyl-1H-1,2,3-triazol-1-yl)-4,6-bis(trifluoromethyl)pyridine constitutes a preferred embodiment of the present invention. Other preferred compounds include 2-(5-phenyl-1H-1,2,3-triazol-1-yl)-6-(trifluoromethyl)pyridine, 2-(5-(4-fluoro)phenyl-1H-1,2,3-triazol-1-yl)-6-(trifluoromethyl)pyridine and 2-(5-(4-fluoro)phenyl-1H-1,2,3-triazol-1-yl)-4,6-bis(trifluoromethyl)pyridine, the latter two being especially preferred compounds.

The active ingredients of the above Formula I are readily prepared employing procedures analogous to the well known procedures used in preparing known substituted 1,2,3-triazole compounds as reviewed by T. L. Gilchrist and G. E. Gymer, Advances in Heterocyclic Chemistry, Vol. 16, p. 33, Academic Press, New York and London, 1974, which is incorporated herein by reference. In general, an appropriately substituted azido compound, i.e., azidopyridine, azidopyrimidine, etc., is reacted with an appropriately substituted acetylene compound to form the active ingredients of Formula I. This reaction can be characterized as follows:

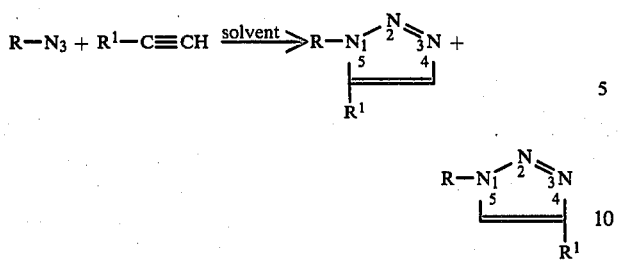

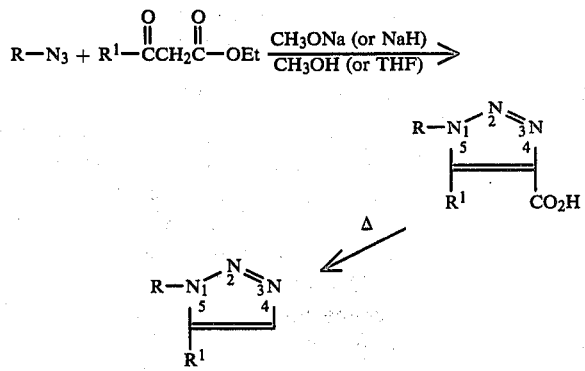

wherein $R^1$ and R are as hereinbefore defined. The resulting product contains both the 1,4 and 1,5 position isomers of the active compounds as indicated in the above reaction.

In carrying out the reaction, the substituted azido compound is advantageously mixed with a solvent, such as, for example, toluene or xylene and then mixed with the substituted acetylene reactant. This reaction mixture is then advantageously heated until the reaction is complete, usually in from about 1 to about 48 hours. The desired products are then recovered using known separatory techniques such as, for example, distillation. If desired, the 1,4 and 1,5 isomers are then separated using known techniques, such as, for example, high pressure liquid chromatography employing an 85:15 hexane/acetone mixture as the eluent. While the amounts of the reactants to be employed are not critical, the reaction generally consumes reactants in the proportion of 1 mole of substituted azido compound reactant to 1 mole of substituted acetylene reactant. A suitable ratio of reactants is from about 1 to 1 to about 1 to 5 (substituted azido compound: substituted acetylene) and the employment of the reactants in a mole ratio of from about 1 to 1.2–2 is preferred. The reaction is usually conducted at temperatures between about 100° C. and 150° C. and is ordinarily carried out at the reflux temperature of the solvent-reactant mixture. Under 100° C. the reaction may proceed but very slowly. A preferred temperature range in which to carry out the present reaction is from about 110° C. to about 130° C. The reaction mixture is usually maintained, with agitation, for a period of time sufficient to provide for substantial completion of the reaction. The reaction is usually conducted at ambient atmospheric pressure.

Alternatively, the substituted 1,2,3-triazoles are prepared by reacting an appropriate azido compound with a β-ketoester in the presence of a strong base, such as, an alkoxide with a corresponding alcohol as a solvent or NaH with a polar solvent, such as tetrahydrofuran (THF) or dimethylformamide (DMF), to yield a substituted 1,2,3-triazole-4-carboxylic acid compound. These substituted 1,2,3-triazole-4-carboxylic acid compounds are novel intermediates and are encompassed by the present invention. Formed in situ is an ester which is hydrolyzed to the carboxylic acid compound by the water which is formed during the cyclization reaction. The esters formed in situ are also novel compounds and are encompassed by the present invention. This carboxylic acid compound is then heated to above its melting point, or at reflux in a high-boiling solvent such as toluene or xylene, which results in the decarboxylation to give the present substituted-1,2,3-triazole. This reaction is characterized as follows:

wherein R and $R^1$ are as hereinbefore described.

A somewhat milder variation of the above procedure may be carried out by employing a tertiary amine, such as triethylamine, as a base in a non-polar solvent, such as methylene chloride or 1,2-dichloroethane, at a temperature of from about 20° C. to about the reflux temperature of the solvent. In this modification, the 1,5-disubstituted triazole-4-carboxylic acid ester is isolated after evaporation of the solvent. This ester is then mildly hydrolyzed to the acid, such as a hydrolysis with potassium hydroxide in 2-propanol. This procedure is characterized as follows:

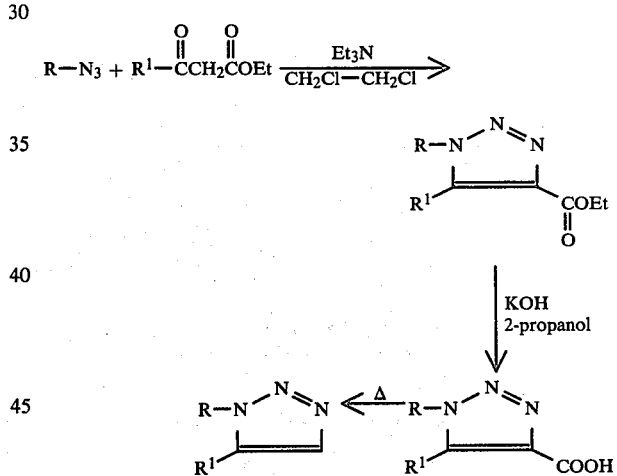

The following examples illustrate the present invention and the manner by which it can be practiced but, as such, are not to be construed as limitations upon the overall scope of the same. No attempt has been made to balance any chemical equations described herein.

EXAMPLE 1

Step A: Preparation of 2-azido-6-(trifluoromethyl)-pyridine

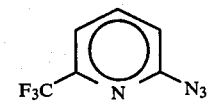

A mixture of 82.5 grams (g) of 2-fluoro-6-(trifluoromethyl)pyridine (0.5 mole), 65 g of sodium azide (1.0 mole) and 400 milliliters (ml) of dimethylsulfoxide (DMSO) was heated to a temperature of 80° C. for 18 hours. The mixture was allowed to cool and then poured into 1500 ml of ice water. This resulting mixture was then extracted 4 times with 300 ml of pentane each time. The pentane extracts were combined, washed with 500 ml of a saturated NaCl solution and dried with MgSO₄. The pentane was then carefully evaporated leaving 67 g of the desired 2-azido-6-(trifluoromethyl)-pyridine as a light yellow oil having an $R_I$ of 1.4771 @25° C.

Step B: Preparation of 2-(4-phenyl-1H-1,2,3-triazol-1-yl)-6-(trifluoromethyl)pyridine and 2-(5-phenyl-1H-1,2,3-triazol-1-yl)-6-(trifluoromethyl)pyridine

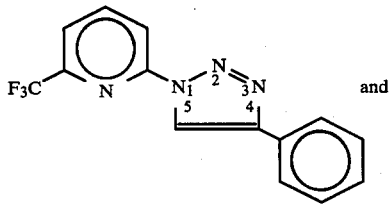

and

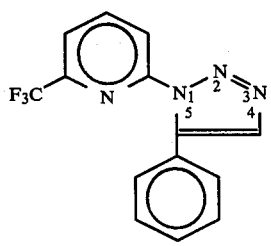

A mixture of 13.5 g of 2-azido-6-(trifluoromethyl)-pyridine (0.072 mole), 12.26 g of phenylacetylene (0.12 mole) and 150 ml of toluene was heated at reflux for 36 hours. The solvent was then evaporated leaving a residual red-brown solid. This solid was purified by preparative high pressure liquid chromatography (HPLC) using an 85:15 hexane/acetone solution as the eluent. Eluting first was 2-(4-phenyl-1H-1,2,3-triazol-1-yl)-6-(trifluoromethyl)pyridine which had a melting point of 142°–144° C. Recrystallization from hexane gave 5.5 g of a white solid which corresponds to a yield of 26 percent of theoretical. Eluting second was 2-(5-phenyl-1H-1,2,3-triazol-1-yl)-6-(trifluoromethyl)-pyridine which had a melting point of 90°–92° C. Recrystallization from hexane gave 6.1 g of a white solid which corresponds to a yield of 29 percent of theoretical. Upon analysis, the 1,5 isomer exhibited a carbon, hydrogen and nitrogen content of 58.01, 3.24 and 19.17 percent, respectively, as compared to the theoretical contents of 57.93, 3.13 and 19.30 percent, respectively. The isomers were identified by their proton n.m.r. according to the criteria given by T. L. Gilchrist and G. E. Gymer, *Advances in Heterocyclic Chemistry*, Vol. 16, p. 33, Academic Press, New York and London, 1974.

EXAMPLE 2

Step A: Preparation of 1-(6-trifluoromethylpyridin-2-yl)-5-(4-pyridyl)1H-1,2,3-triazole-4-carboxylic Acid

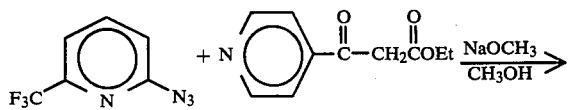

-continued

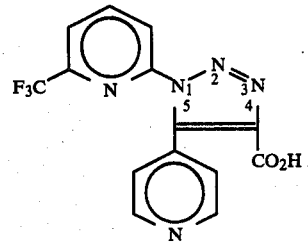

A reaction mixture of sodium methoxide (3.24 grams (g), 0.06 mole), 2-azido-6-trifluoromethylpyridine (9.4 g, 0.05 mole), ethyl (isonicotinoyl)-acetate (8.95 g; 0.05 mole) and methanol (200 milliliters (ml)) was heated, with stirring, at reflux for 7 hours. The mixture was then cooled and the methanol evaporated. The residue was then added to 600 ml of warm water, acidified with 5 ml of concentrated hydrochloric acid and then allowed to stand overnight. A precipitate formed which was filtered, washed with several portions of water, and dried in a vacuum oven to give 12 g of the crude carboxylic acid intermediate which melted at 206° C. with vigorous gas evolution. This carboxylic acid intermediate was then decarboxylated without further purification as described in Step B' below.

Step B': Preparation of 1-(6-trifluoromethylpyridin-2-yl)-5-(4-pyridyl)-1,2,3-triazole

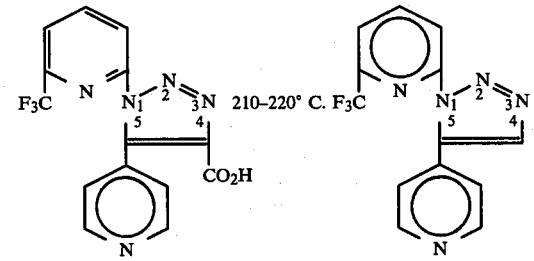

The 1-(6-trifluoromethylpyridin-2-yl)-5-(4-pyridyl)-1,2,3-triazole-4-carboxylic acid (12 g; 0.036 mole), formed in Step C above, was placed in a 100 ml round bottom flask which was partially immersed in an oil bath that was heated to a temperature between 210°–220° C. As the carboxylic acid intermediate melted, gas evolution occurred. When the gas evolution ceased (approximately 5 minutes) the heat was removed and 85 ml of tetrahydrofuran was added to the flask. The resulting solution was filtered to remove some insoluble material and then the solvent was evaporated to give 7.4 g of a brown solid. This brown solid was then recrystallized from methylcyclohexane to give 6.8 g of a tan solid that had a melting point of 130.5°–134° C. An analytical sample was prepared by recrystallizing the tan solid in a small volume of toluene which gave a product that had a melting point of 132°–134° C. Upon analysis, the prepared compound exhibited a carbon, hydrogen and nitrogen content of 53.58, 2.81 and 24.09 percent, respectively, as compared to the theoretical contents of 53.61, 2.77 and 24.05 percent, respectively, calculated for 1-(6-trifluoromethylpyridin-2-yl)-5-(4-pyridyl)-1,2,3-triazole.

EXAMPLE 3"

Preparation of 1-(6-trifluoromethylpyridin-2-yl)-5-methyl-1,2,3-tiazole

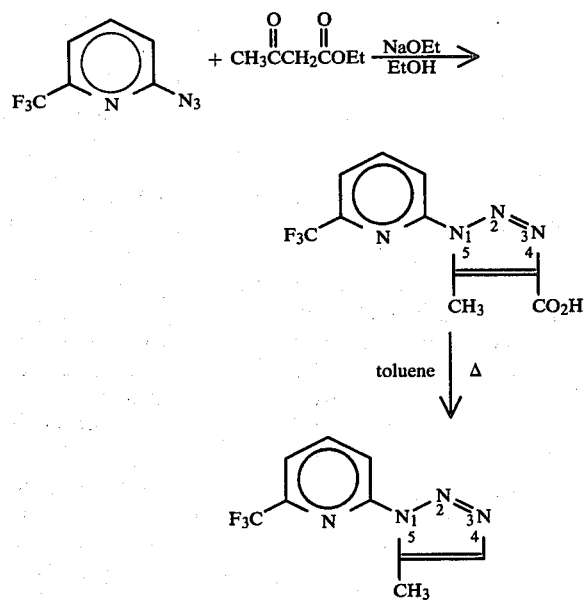

To a solution of sodium ethoxide (from 0.96 g (0.04 mole) of sodium) in 125 ml ethanol was added ethyl acetoacetate (5.21 g; 0.04 mole) and 2-azido-6-trifluoromethylpyridine (7.52 g; 0.04 mole). The solution was heated at reflux for 3 hours. During this period a solid precipitated from the solution. The solution was then poured into 800 ml water and acidified with 10 ml of concentrated hydrochloric acid. A solid precipitated out of solution which was filtered, washed with several portions of water and then air dried. The resulting white powder was then heated at reflux in toluene for 20 minutes. The toluene was then evaporated and the residue was recrystallized from hexane to give a light yellow solid (4.2 g) that had a melting point of 67°–68° C. Upon analysis, the prepared compound exhibited a carbon, hydrogen and nitrogen content of 47.67, 3.26 and 24.63 percent, respectively, as compared to the theoretical contents of 47.37, 3.09 and 24.56 percent, respectively, calculated for 1-(6-trifluoromethylpyridin-2-yl)-5-methyl-1,2,3-triazole.

EXAMPLE 4

Step A": Preparation of 2-(4-carboxylic acid)-(5-(4-fluoro)-phenyl-1H-1,2,3-triazol-1-yl)-4,6-bis(trifluoromethyl)pyridine, ethyl ester

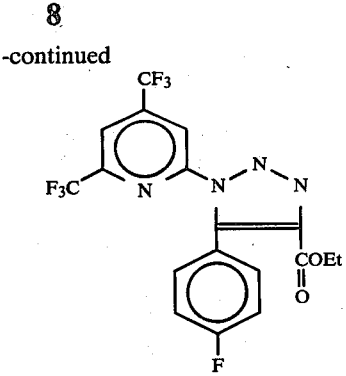

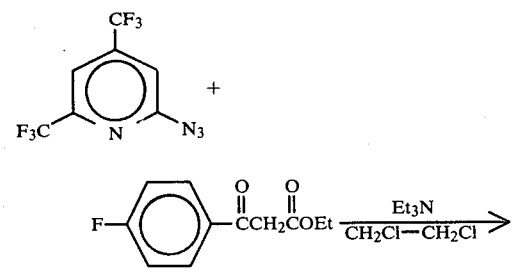

A stirred solution of 2-azido-4,6-bis(trifluoromethyl)-Pyridine (140.87 g, 0.55 mole), ethyl 4-fluorobenzoylacetate (115.61 g, 0.55 mole) and triethylamine (56.6 g, 0.56 mole) in 1,2-dichloroethane (600 ml) was heated at reflux for 6 hours. The apparatus was equipped such that the condensate passed through a Soxhlet extractor containing 3 A molecular sieves. In this manner, the water which was formed during the reaction was continuously removed. At the end of the reaction period, the mixture was cooled, and the solvent evaporated. The yellow-white residual solid was recrystallized from methyl cyclohexane to give 205 g (83%) of the desired triazole derivative.

Step B": Preparation of 2-(4-carboxylic acid)-(5-(4-fluoro)phenyl-1H-1,2,3-triazol-1-yl)-4,6-bis(trifluoromethyl)pyridine

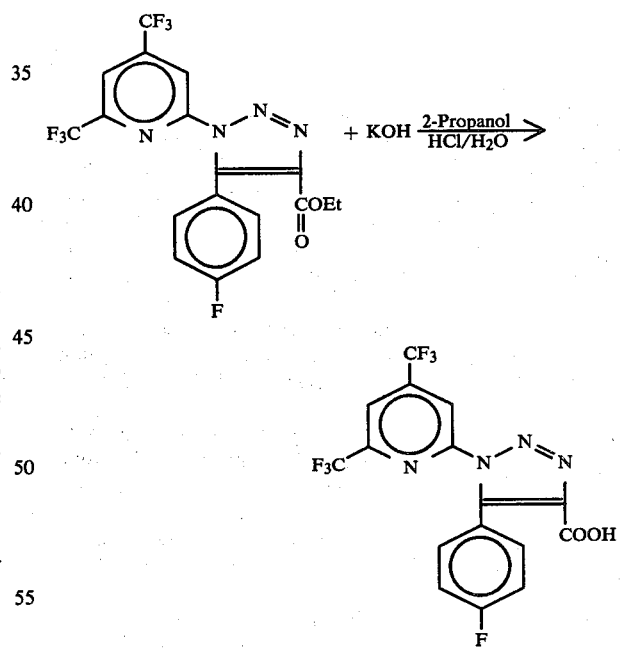

To a mechanically stirred solution of potassium hydroxide (60.33 g of 85% KOH, 0.914 mole) in 2-propanol (1500 ml) which was cooled to 5° C. via an ice-bath, was added, all at once, the triazole-4-carboxylic acid ester (205 g, 0.457 mole) of Step A. Initially, most of the ester dissolved, but soon a thick, almost gelataneous solid began to separate. The mixture was vigorously stirred at 5° for 15 min, then at room temperature for 3 hours. After the hydrolysis was complete, the reaction mixture was poured into water (4000 ml)

and acidified with concentrated hydrochloric acid (100 ml). The aqueous mixture was saturated with sodium chloride, then extracted with ether (3×500 ml). The organic phases were combined, washed with saturated sodium choloride solution, dried (MgSO₄) and the solvent evaporated to give the desired acid as a white solid. An analytical sample was obtained by recrystallization from ether-hexane. The product had a melting point of 146° C. with decomposition. Upon analysis, the prepared compound exhibited a carbon, hydrogen and nitrogen content of 45.77, 1.60 and 13.42 percent, respectively, as compared to the theoretical contents of 45.73, 1.68 and 13.33 percent, respectively, calculated for 2-(4-carboxylic acid)-(5-(4-fluoro)-phenyl-11H-1,2,3-triazol-1-yl)-4,6-bis(trifluoromethyl)pyridine.

Step C″: Preparation of 2-(5-(4-fluoro)phenyl- 1H-1,2,3-triazol-1-yl)-4,6-bis(trifluoromethyl)pyridine

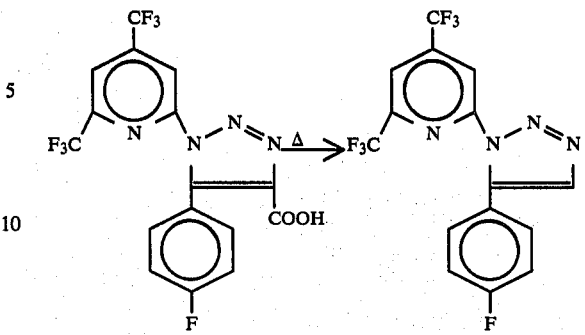

The 4-carboxylic acid pyridine compound produced in Step B above is then heated above its melting point to yield the desired 2-(5-(4-fluoro)phenyl-1H-1,2,3-triazol-1-yl)-4,6-bis(trifluoromethyl)pyridine.

EXAMPLE 5

In substantial accordance with the procedures of Examples 1-4 and employing the appropriate starting materials, the compounds listed in Table I were prepared:

TABLE I

| Compound | Melting Point | Analysis Calculated | Found |
|---|---|---|---|
| 1. 4-(5-phenyl-1H—1,2,3-triazol-1-yl)-2,6-bis(trifluoromethyl)pyridine | 141.5–143.5° (methylcyclohexane) | C 50.29<br>H 2.25<br>N 15.64 | C 50.14<br>H 2.23<br>N 15.73 |
| 2. 2-(5-phenyl-1H—1,2,3-triazol-1-yl)-4-(trifluoromethyl)pyridine | 167–168° (methylcyclohexane) | C 57.93<br>H 3.13<br>N 19.31 | C 57.79<br>H 3.17<br>N 19.60 |
| 3. 4-(5-phenyl-1H—1,2,3-triazol-1-yl)-2-(trifluoromethyl)pyridine | 105–106.5° (hexane) | C 57.93<br>H 3.13<br>N 19.31 | C 57.47<br>H 3.22<br>N 19.23 |
| 4. 2-(5-phenyl-1H—1,2,3-triazol-1-yl)-4,6-bis(trifluoromethyl)pyridine | 102.5–104° (hexane) | C 50.29<br>H 2.25<br>N 15.64 | C 50.20<br>H 2.24<br>N 15.54 |
| 5. 2-(5-methyl-1H—1,2,3-triazol-1-yl)-6-(trifluoromethyl)pyridine | 67–68° (hexane) | C 47.37<br>H 3.09<br>N 24.56 | C 47.67<br>H 3.26<br>N 24.63 |
| 6. 2-(5-cyclopropyl-1H—1,2,3-triazol-1-yl)-6-(trifluoromethyl)pyridine | 89–91° (hexane) | C 51.97<br>H 3.57<br>N 22.04 | C 51.94<br>H 3.57<br>N 22.02 |
| 7. 2-(5-phenyl-1H—1,2,3-triazol-1-yl)-6-(fluoro)pyridine | 120–122° (ether-pentane) | C 64.99<br>H 3.78<br>N 23.32 | C 64.95<br>H 3.82<br>N 23.58 |
| 8. 2-(5-phenyl-1H—1,2,3-triazol-1-yl)-6-(oxy-2,4-dichlorophenyl)pyridine | 89–90° (hexane-ether) | C 59.54<br>H 3.16<br>N 14.62 | C 59.38<br>H 3.21<br>N 19.93 |
| 9. 2-(5-phenyl-1H—1,,2,3-triazol-1-yl)-6-(chloro)pyridine | 127–129° (hexane-ether) | C 60.82<br>H 3.53<br>N 21.83 | C 60.54<br>H 3.51<br>N 22.03 |
| 10. 2-(5-phenyl-1H—1,2,3-triazol-1-yl)-4-(trifluoromethyl)pyrimidine | 96.5–100° (hexane-methylene chloride) | C 53.61<br>H 2.77<br>N 24.05 | C 53.44<br>H 2.87<br>N 23.93 |
| 11. 2-(5-(2-pyridyl)-1H—1,2,3-triazol-1-yl)-6-(trifluoromethyl)pyridine | 127–128° (methylcyclohexane) | C 53.61<br>H 2.77<br>N 24.05 | C 53.40<br>H 2.77<br>N 24.00 |
| 12. 2-(5-(3-pyridyl)-1H—1,2,3-triazol-1-yl)-6-(trifluoromethyl)pyridine | 109–111° (methylcyclohexane-benzene) | C 53.61<br>H 2.77<br>N 24.05 | C 53.57<br>H 2.78<br>N 24.00 |
| 13. 4-(5-phenyl-1H—1,2,3-triazol-1-yl)-6-(trifluoromethyl)pyrimidine | 55–57° (ether-pentane) | C 53.61<br>H 2.77<br>N 24.05 | C 53.78<br>H 2.72<br>N 23.98 |
| 14. 2-(5-(4-pyridyl)-1H—1,2,3-triazol-1-yl)-6-(trifluoromethyl)pyridine | 132–134° (toluene) | C 53.61<br>H 2.77<br>N 24.05 | C 53.58<br>H 2.81<br>N 24.09 |
| 15. 4-(5-phenyl-1H—1,2,3-triazol-1-yl)-2-(trifluoromethyl)pyrimidine | 95–97° (hexane) | C 53.61<br>H 2.77<br>N 24.05 | C 53.25<br>H 3.36<br>N 24.03 |
| 16. 2-(5-(2-thiophene)-1H—1,2,3-triazol-1-yl)-6-(trifluoromethyl)pyridine | 70–71° (ether-hexane) | C 48.64<br>H 2.38<br>N 18.91 | C 48.48<br>H 2.29<br>N 19.27 |
| 17. 2-(5-phenyl-1H—1,2,3-triazol-1-yl)- | 115–116° C. | C 51.78 | C 51.49 |

TABLE I-continued

| Compound | Melting Point | Analysis Calculated | Found |
|---|---|---|---|
| 4-trifluoromethyl-6-(chloro)pyridine | (hexane) | H 2.48<br>N 17.26 | H 2.45<br>N 17.42 |
| 18. 4-(5-phenyl-1H—1,2,3-triazol-1-yl)-2-trifluoromethyl-6-(chloro)pyridine | 132.5–134.5° C.<br>(methylcyclohexane) | C 51.78<br>H 2.48<br>N 17.26 | C 51.80<br>H 2.41<br>N 17.41 |
| 19. 2-(5-phenyl-1H—1,2,3-triazol-1-yl)-4-chloro-6-(trifluoromethyl)pyridine | 73–75° C.<br>(hexane) | C 51.78<br>H 2.48<br>N 17.26 | C 51.66<br>H 2.41<br>N 17.44 |
| 20. 4-(5-phenyl-1H—1,2,3-triazol-1-yl)-2,6-(dichloro)pyridine | 99–101° C.<br>(hexane-methylene chloride) | C 53.63<br>H 2.77<br>N 19.25 | C 53.77<br>H 2.89<br>N 19.01 |
| 21. 2-(5-phenyl-1H—1,2,3-triazol-1-yl)-4,6-(dichloro)pyridine | 93–94° C.<br>(hexane-ether | C 53.63<br>H 2.77<br>N 19.25 | C 53.57<br>H 2.75<br>N 19.14 |
| 22. 2-(5-(4-chloro)phenyl-1H—1,2,3-triazol-1-yl)-6-(trifluoromethyl)pyridine | 113–115° C.<br>(hexane-ether) | C 51.78<br>H 2.48<br>N 17.26 | C 51.772<br>H 2.60<br>N 17.29 |
| 23. 2-(5-(4-methoxy)phenyl-1H—1,2,3-triazol-1-yl)-6-(trifluoromethyl)pyridine | 116–117° C.<br>(ether-hexane) | C 56.25<br>H 3.46<br>N 17.49 | C 55.93<br>H 3.42<br>N 17.48 |
| 24. 2-(5-(4-fluoro)phenyl-1H—1,2,3-triazol-1-yl)-6-(trifluoromethyl)pyridine | 118–120° C.<br>(hexane-ether | C 54.55<br>H 2.62<br>N 18.18 | C 54.56<br>H 2.61<br>N 18.15 |
| 25. 2-(5-(4-methyl)phenyl-1H—1,2,3-triazol-1-yl)-6-(trifluoromethyl)pyridine | 88–90° C.<br>(hexane-ether) | C 59.21<br>H 3.64<br>N 18.41 | C 59.10<br>H 3.53<br>N 18.44 |
| 26. 2-(5-(2-fluoro)phenyl-1H—1,2,3-triazol-1-yl)-6-(trifluoromethyl)pyridine | 87–89° C.<br>(hexane-acetone) | C 54.55<br>H 2.62<br>N 18.18 | C 54.56<br>H 2.61<br>N 18.15 |
| 27. 2-(5-phenyl-1H—1,2,3-triazol-1-yl)-6-bromopyridine | 109.5–111° C.<br>(methylcyclohexane) | C 51.84<br>H 3.01<br>N 18.61 | C 51.52<br>H 2.98<br>N 18.58 |
| 28. 2-(5-phenyl-1H—1,2,3-triazol-1-yl)-6-chloropyrazine | 75–77.5° C.<br>(hexane-ether) | C 55.93<br>H 3.13<br>N 27.18 | C 55.55<br>H 3.09<br>N 27.33 |
| 29. 2-(5-phenyl-1H—1,2,3-triazol-1-yl)-6-isopropylpyrimidine | oil<br>Refractive index = 1.5863 | | |
| 30. 2-(5-(3-fluoro)phenyl-1H—1,2,3-triazol-1-yl)-6-(trifluoromethyl)pyridine | 82–83.5° C.<br>(ether-pentane) | C 54.55<br>H 2.62<br>N 18.18 | C 54.50<br>H 2.55<br>N 18.36 |
| 31. 2-(5-(4-trifluoromethyl)phenyl-1H—1,2,3-triazol-1-yl)-6-(trifluoromethyl)pyridine | 89–90.5° C.<br>(ether-hexane) | C 50.29<br>H 2.25<br>N 15.64 | C 49.99<br>H 2.07<br>N 15.83 |
| 32. 2-(5-(3-trifluoromethyl)phenyl-1H—1,2,3-triazol-1-yl)-6-(trifluoromethyl)pyridine | oil<br>Refractive index = 1.5200 | | |

The compounds of the present invention have been found to be suitable for use in methods for the preemergent and postemergent control of annual grasses, such as barnyard grass, crabgrass, yellow foxtail and wild oats, perennial grasses, such as johnson grass, and broadleaf weeds, such as morning glory and velvetleaf, in the presence of the seeds or seedling plants of broadleaf crops, such as cotton, and soybeans. The 4-isomer, i.e., compounds having the substituent $R^1$ in the 4 triazole ring position, are inactive as herbicidal agents. In the practice of the present invention, the 5-isomer alone is preferred but a mixture of the 4 and 5 isomers can be used to control the aforementioned plants.

Preferred herbicidal compounds of the present invention include compounds of the formula:

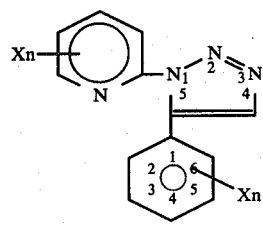

(II)

wherein X and n are as defined hereinbefore. Especially preferred compounds include those of the above Formula II wherein the pyridine ring, attached to the 1-position of the triazole ring, optionally contains 1 or 2-$CF_3$ groups in the 4- and/or 6-position of the pyridine ring and the phenyl ring, attached to the 5-position of the triazole ring, optionally contains a fluoro atom in the 4-position of the phenyl ring.

For herbicidal use, unmodified active ingredients of the present invention can be employed. However, the present invention embraces the use of a herbicidally-effective amount of the active ingredients in composition form with an inert material known in the art as an adjuvant or carrier in solid or liquid form. Thus, for example, an active ingredient can be dispersed on a finely divided solid and employed therein as a dust. Also, the active ingredients, as liquid concentrates or solid compositions comprising one or more of the active ingredients, can be dispersed in water, typically with the aid of a wetting agent, and the resulting aqueous dispersion employed as a spray. In other procedures, the active ingredient can be employed as a constituent of organic liquid compositions, oil-in-water and water-in-oil emulsions, or water dispersions, with or without the addition of wetting, dispersion, or emulsifying agents.

Suitable adjuvants of the foregoing type are well-known to those skilled in the art. The methods of applying the solid or liquid herbicidal formulations similarly are well known to the skilled artisan.

As organic solvents used as extending agents there can be employed hydrocarbons, e.g., benzene, toluene, xylene, kerosene, diesel fuel, fuel oil, and petroleum naphtha; glycol ethers; paraffinic oils, cyclohexanone, Tenneco ® and alcohols. Mixtures of water and organic solvents, either as solutions or emulsions, can be employed.

The active ingredients of the present invention can also be applied with solid adjuvants or carriers such as talc, pyrophyllite, synthetic fine silica, attapulgus clay, kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character.

Typical classes of surface active agents include fatty acid alcohol sulfates, fatty acid ethoxylate sulfates, dodecyl benzene sulfonates, phosphate esters, alcohol ethoxylates and ethylene oxide-propylene oxide block copolymers.

The concentration of the active ingredients in solid or liquid compositions generally is from about 0.001 to about 95 percent by weight or more. Concentrations of from about 0.003 to about 50 weight percent are often employed. In compositions to be employed as concentrates, the active ingredient can be present in a concentration of from about 5 to about 98 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

The present compositions can be applied by the use of power-dusters, boom and hand sprayers, spray-dusters, by addition to irrigation water, and by other conventional means. The compositions can also be applied from airplanes as a dust or a spray since certain of the active ingredients are effective at low applications rates.

The exact rate to be applied is dependent not only upon the specific active ingredient being employed, but also upon the stage of growth thereof as well as the part of the plants to be contacted with the toxic active ingredient. Thus, it is to be understood that all of the active ingredients of the invention and compositions containing the same may not be equally effective at similar concentrations. In selective pre- and early postemergence operations, a dosage of from about 0.05 to about 20 pounds per acre is usually employed but about 0.05 to about 2 pounds per acre is a preferred rate. In view of the foregoing and following disclosures, one skilled in the art can readily determine the optimum rate to be applied in any particular case.

In a representative operation, each compound to be utilized in a series of tests is dissolved in acetone to ½ the final volume to be used and the acetone solution in each case is then admixed with an equal volume of water containing 0.1 percent by weight of TWEEN ®-20 surfactant, a commercially available product from Atlas Chemical Company. Each compound is an active compound of Formula I. The compositions, generally in the nature of an emulsion, are employed to treat separate respective seed beds of agricultural soil of good nutrient content wherein each seed bed contains separate groups of good, viable seeds. The various beds are positioned side by side and exposed to substantially identical conditions of temperature and light. Each bed is maintained so as to prevent any interaction with test compounds in different seed beds. Each seed bed is treated with one of the compositions as a soil drench applied uniformly throughout the surface of the bed using predetermined amounts of a given test compound. The compositions are applied so that respectively different seed beds are treated with one of each of the test compounds. Another seed bed is treated only with water to serve as a control. After treatment, the seed beds are maintained for two to three weeks under greenhouse conditions conducive for good plant growth and watered as necessary. The specific plant species, test compound and dosage and the percent control obtained are set forth in Table II below. Percent control refers to the reduction in growth compared to the observed growth of the controls.

TABLE II

| Active Compound | Dosage In lb/acre | Percent Control of | | | | |
|---|---|---|---|---|---|---|
| | | Barnyard Grass | Crabgrass | Yellow Foxtail | Johnson Grass | Velvet Leaf |
| Control (No Active Compound) | None | 0 | 0 | 0 | 0 | 0 |
| 2-(5-(4-fluoro)phenyl-1H—1,2,3-triazol-1-yl)-4,6-bis(trifluoromethyl)pyridine | 10 | 100 | 100 | 100 | NR* | 90 |
| 2-(5-(4-fluoro)phenyl-1H—1,2,3-triazol-1-yl)-6-(trifluoromethyl)-pyridine | 10 | 100 | 100 | 100 | NR* | 80 |
| 2-(5-phenyl-1H—1,2,3-triazol-1-yl)-4,6-bis(trifluoromethyl)pyridine | 0.125 | 100 | 100 | 100 | 100 | 10 |
| 2-(5-phenyl-1H—1,2,3-triazol-1-yl)-6-(trifluoromethyl)pyridine | 0.25 | 98 | 97 | 98 | 95 | 20 |
| 4-(5-phenyl-1H—1,2,3-triazol-1-yl)-2-(trifluoromethyl)pyridine | 10 | 100 | 100 | 100 | NR* | 10 |
| 2-(5-cyclopropyl-1H—1,2,3-triazol- | 10 | 100 | 100 | 100 | NR* | 30 |

TABLE II-continued

| Active Compound | Dosage In lb/acre | Percent Control of | | | | |
|---|---|---|---|---|---|---|
| | | Barnyard Grass | Crabgrass | Yellow Foxtail | Johnson Grass | Velvet Leaf |
| 1-yl)-6-(trifluoromethyl)pyridine | | | | | | |
| 2-(5-(2-pyridyl)-1H—1,2,3-triazol-1-yl)-6-(trifluoromethyl)pyridine | 10 | 100 | 100 | 100 | NR* | NR* |
| 2-(5-(3-pyridyl)-1H—1,2,3-triazol-1-yl)-6-(trifluoromethyl)pyridine | 10 | 100 | 100 | 98 | NR* | NR* |
| 4-(5-phenyl-1H—1,2,3-triazol-1-yl)-2-(trifluoromethyl)pyridmidine | 10 | 100 | 100 | 100 | NR* | 40 |
| 2-(5-phenyl-1H—1,2,3-triazol-1-yl)-6-(fluoro)pyridine | 10 | 100 | 100 | 100 | NR* | 85 |
| 2-(5-phenyl-1H—1,2,3-triazol-1-yl)-6-(chloro)pyridine | 10 | 100 | 100 | 100 | NR* | 85 |
| 2-(5-phenyl-1H—1,2,3-triazol-1-yl)-4-trifluoromethyl-6-(chloro)pyridine | 10 | 100 | 100 | 100 | NR* | 100 |
| 2-(5-phenyl-1H—1,2,3-triazol-1-yl)-4-chloro-6-(trifluoromethyl)pyridine | 10 | 100 | 100 | 100 | NR* | 90 |
| 4-(5-phenyl-1H—1,2,3-triazol-1-yl)-2,6-(dichloro)pyridine | 10 | 0 | 100 | 100 | NR* | 0 |
| 2-(5-phenyl-1H—1,2,3-triazol-1-yl)-4,6-(dichloro)pyridine | 10 | 100 | 100 | 100 | NR* | 0 |
| 2-(5-phenyl-1H—1,2,3-triazol-1-yl)-4-(trifluoromethyl)pyrimidine | 10 | 98 | 100 | 98 | NR* | 60 |
| 2-(5-(2-thiophene)-1H—1,2,3-triazol-1-yl)-6-(trifluoromethyl)pyridine | 10 | 100 | 100 | 100 | NR* | 70 |
| 2-(5-(4-chloro)phenyl-1H—1,2,3-triazol-1-yl)-6-(trifluoromethyl)-pyridine | 10 | 100 | 100 | 100 | NR* | 80 |
| 2-(5-(4-methyl)phenyl-1H—1,2,3-triazol-1-yl)-6-(trifluoromethyl)pyridine | 10 | 100 | 100 | 100 | NR* | 40 |
| 2-(5-(2-fluoro)phenyl-1H—1,2,3-triazol-1-yl)-6-(trifluoromethyl)pyridine | 10 | 100 | 100 | 100 | NR* | 80 |
| 2-(5-phenyl-1H—1,2,3-triazol-6-(chloro)pyrazine | 10 | 60 | 100 | 98 | NR* | 0 |
| 2-(5-(3-fluoro)phenyl-1H—1,2,3-triazol-1-yl)-6-(trifluoromethyl)-pyridine | 10 | 100 | 100 | 100 | NR* | 100 |
| 2-(5-phenyl-1H—1,2,3-triazol-1-yl)-6-bromopyridine | 10 | 100 | 100 | 100 | NR* | 95 |
| 2-5-(4-trifluoromethyl)phenyl-1H—1,2,3-triazol-1-yl)-6-(trifluoromethyl)-pyridine | 10 | 100 | 100 | 80 | NR* | 0 |
| 2-(5-(3-trifluoromethyl)phenyl-1H—1,2,3-triazol-1-yl)-6-(trifluoromethyl)-pyridine | 10 | 100 | 100 | 98 | NR* | 20 |

*NR denotes "not run"

EXAMPLE 6

Forty-five (45) parts by weight of 2-(5-phenyl-1H-1,2,3-triazol-1-yl)-4,6-bis(trifluoromethyl)pyridine is mixed and ground with 5 parts by weight of TRITON®X-155 surfactant (an alkylated aryl polyether alcohol) to prepare a water-dispersible concentrate composition containing 90 percent by weight of the active compound.

In a further operation, 25 parts by weight of 2-(5-phenyl-1H-1,2,3-trazol-1-yl)-4,6-bis(trifluoromethyl)pyridine, 10 parts by weight of TRITON®X-155 surfactant and 65 parts by weight of xylene are mixed together to prepare an emulsifiable concentrate composition containing 25 percent by weight of said active compound.

In another operation, the following ingredients were mixed to form a 10 percent emulsifiable concentrate of 2-(5-phenyl-1H-triazol-1-yl)-6-(chloro)pyridine which is applied to undesirable plants as an emulsion when diluted in water:

| | |
|---|---|
| 2-(5-phenyl-1H—1,2,3-triazol-1-yl)-6-(chloro)pyridine | 10% (by weight) |
| CH₂Cl₂ | 40% |
| cyclohexanone | 21% |
| SC-100 (high flash aromatics) | 19% |
| EMCOLL® P10-20 | 5% |
| ATLOX® 8916P | 5% |
| | 100% |

The concentrate compositions thus prepared can be dispersed in water to prepare aqueous compositions which have very desirable wetting and penetrating properties and are adapted to distribute growth inhibiting amounts of the active compounds on plant parts.

Representative compositions of the present invention were evaluated for the post-emergence control of species of plants listed in Table A. In these evaluations, plots of the plant species listed in Table A, grown to a height of about 4 inches, were used. Aqueous spray compositions, each containing 4,000 parts of a given active compound per million parts of ultimate composition, were prepared in accordance with the procedures of Example 5, and each separate composition was applied to a separate plot. The application was made to the point of run-off and was carried out with conventional spraying equipment. Other plots were sprayed with similar compositions containing no toxicant to serve as controls. Thereafter, the plots were maintained under conditions conducive for plant growth. Two weeks after treatment, the plots were examined for plant growth and evaluated. The results of the examination of the treated plots are set forth below in Table A.

tericides that are compatible with the compounds of the present invention in the medium selected for application and antagonistic to the activity of the present compounds. Accordingly, in such embodiments, the pestici-

TABLE A

| Active Compound Employed | Percent Kill and Control of | | | | | | | | |
|---|---|---|---|---|---|---|---|---|---|
| | Barnyard Grass | Wild Oats | Crab-Grass | Pig-weed | Yellow Foxtail | Yellow Nutsedge | Morning Glory | Velvet Leaf | Cotton |
| None | 0 | 0 | 0 | 0 | 0 | 0 | 0 | 0 | 0 |
| 2-(5-(4-fluoro)phenyl-1H—1,2,3-triazol-1-yl)-4,6-bis(trifluoromethyl)pyridine | 90 | 90 | 95 | NR* | 95 | 0 | 80 | 80 | 20 |
| 2-(5-(4-fluoro)phenyl-1H—1,2,3-triazol-1-yl)-6-(trifluoromethyl)pyridine | 80 | 50 | 70 | 50 | 70 | 70 | 50 | 100 | 80 |
| 2-(5-phenyl-1H—1,2,3-triazol-1-yl)-4,6-bis(trifluoromethyl)pyridine | 80 | 80 | 90 | NR* | 90 | 0 | 70 | 70 | 30 |
| 2-(5-phenyl-1H—1,2,3-triazol-1-yl)-6-(trifluoromethyl)pyridine | 80 | 50 | 80 | 0 | 80 | 50 | 80 | 50 | 80 |
| 4-(5-phenyl-1H—1,2,3-triazol-1-yl)-2-(trifluoromethyl)pyridine | 20 | 0 | 100 | 80 | 60 | 0 | 0 | NR | 0 |
| 2-(5-methyl-1H—1,2,3-triazol-1-yl)-6-(trifluoromethyl)pyridine | 0 | 0 | 80 | 0 | 10 | 0 | 0 | 0 | 0 |
| 2-(5-cyclopropyl-1H—1,2,3-triazol-1-yl)-6-(trifluoromethyl)pyridine | 0 | 0 | 20 | 0 | 0 | 0 | 0 | 10 | 0 |
| 2-(5-phenyl-1H—1,2,3-triazol-1-yl)-4-(trifluoromethyl)pyrimidine | 0 | 0 | 45 | 50 | 15 | 0 | 20 | 35 | 25 |
| 2-(5-(2-pyridyl)-1H—1,2,3-triazol-1-yl)-6-(trifluoromethyl)pyridine | 40 | 65 | 90 | 0 | 80 | 0 | 40 | 0 | 0 |
| 2-(5-(4-pyridyl)-1H—1,2,3-triazol-1-yl)-6-(trifluoromethyl)pyridine | 0 | 0 | 50 | 50 | 0 | 0 | 0 | 0 | 0 |
| 2-(5-phenyl-1H—1,2,3-triazol-1-yl)-6-(fluoro)pyridine | 70 | 40 | 0 | 0 | 0 | 0 | 50 | 50 | 10 |
| 2-(5-phenyl-1H—1,2,3-triazol-1-yl)-6-(chloro)pyridine | 60 | 60 | 90 | NR | 85 | 0 | 75 | 50 | 10 |
| 2-(5-phenyl-1H—1,2,3-triazol-1-yl)-4-trifluoromethyl-6-(chloro)pyridine | 90 | 80 | 95 | 80 | 95 | 0 | 90 | 85 | 50 |
| 2-(5-phenyl-1H—1,2,3-triazol-1-yl)-4-chloro-6-(trifluoromethyl)pyridine | 80 | 80 | 90 | 50 | 90 | 0 | 0 | 60 | 60 |
| 4-(5-phenyl-1H—1,2,3-triazol-1-yl)-2,6-(dichloro)pyridine | 0 | 0 | 0 | 0 | 0 | 0 | 0 | 0 | 0 |
| 2-(5-phenyl-1H—1,2,3-triazol-1-yl)-4,6-(dichloro)pyridine | 70 | 60 | 80 | 70 | 80 | 30 | 15 | 60 | 80 |
| 2-(5-(4-chloro)phenyl-1H—1,2,3-triazol-1-yl)-6-(trifluoromethyl)pyridine | 90 | 70 | 90 | 0 | 90 | 0 | 80 | 75 | 100 |
| 2-(5-(4-methyl)phenyl-1H—1,2,3-triazol-1-yl)-6-(trifluoromethyl)pyridine | 90 | 20 | 80 | 20 | 70 | NR | 20 | 50 | 80 |
| 2-(5-(2-fluoro)phenyl-1H—1,2,3-triazol-1-yl)-6-(trifluoromethyl)pyridine | 90 | 60 | 95 | 100 | 90 | 55 | 95 | 60 | NR |
| 2-(5-phenyl-1H—1,2,3-triazol-1-yl)-6-chloropyrazine | 60 | 0 | 80 | 0 | 85 | 0 | 0 | 25 | 40 |
| 2-(5-(2-thiophene)-1H—1,2,3-triazol-1-yl)-6-(trifluoromethyl)pyridine | 0 | 40 | 50 | 60 | 50 | 0 | 20 | 50 | 20 |
| 2-(5-(3-fluoro)phenyl-1H—1,2,3-triazol-1-yl)-6-(trifluoromethyl)pyridine | 80 | 80 | 100 | 100 | 90 | 0 | 80 | 80 | 70 |
| 2-(5-phenyl-1H—1,2,3-triazol-1-yl)-6-bromopyridine | 80 | 20 | 85 | 20 | 85 | 50 | 25 | 55 | 80 |

*NR denotes "not run"

When applied at a dosage rate of from about 0.05 to about 20 pounds per acre, each of the compounds of the present invention, the utility of which is not specifically exemplified above, has the ability to kill and control one or more of the hereinabove listed pests as well as other pests of the same class or classes.

In further embodiments, the compounds of the present invention or compositions containing the same, can be advantageously employed in combination with one or more additional pesticidal compounds. Such additional pesticidal compounds may be insecticides, nematocides, arthropodicides, herbicides, fungicides or bactericides that are compatible with the compounds of the present invention in the medium selected for application and antagonistic to the activity of the present compounds. Accordingly, in such embodiments, the pesticidal compound is employed as a supplemental toxicant for the same or for a different pesticidal use, or as an additament. The compounds in combination can generally be present in the ratio of from 1 to 100 parts of the compound of the present invention with from 100 to 1 parts of the additional compound(s).

Starting Materials

The azido compounds employed as starting materials in the preparation of the present compounds can be prepared by any of several standard methods known in the art. See, for example, J. March, *Advanced Organic Chemistry: Reactions, Mechanisms, and Structure*, p. 965, McGraw-Hill Book Co., New York, 1968, which is incorporated herein by reference. Two of such known methods are exemplified below. In one such method the displacement of an activated leaving group, i.e., halogen or methylsulfonyl group, from a heterocyclic ring occurs using sodium azide and DMSO or sulfolane as a solvent. This reaction is carried out at a temperature of from about 25° C. to about 150° C. See Example 1, Step A. In the second method an aromatic hydrazine is reacted with nitrous acid to give the desired azide.

EXAMPLE 7

Preparation of 2-azido-6-(trifluoromethyl)pyridine

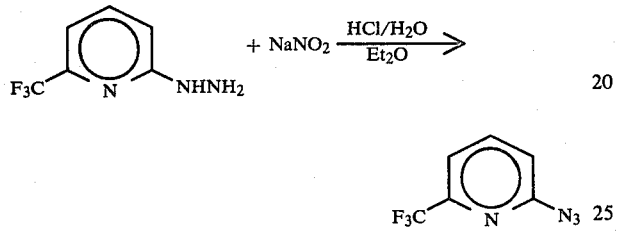

To a cold (~5° C.) mechanically stirred mixture of concentrated hydrochloric acid (300 ml), water (1000 ml), ether (500 ml) and 2-hydrazino-6-(trifluoromethyl)-pyridine (168.27 g, 0.95 mole) was slowly added a solution of sodium nitrite (72.15 g, 1.05 moles) in water (100 ml). This addition took about 75 minutes while the reaction temperature was kept at ≦9° C. After the addition was complete, stirring was continued for 1 hour at ice-bath temperatures; then the organic phase was separated. The aqueous phase was extracted with additional ether (2×200 ml). The organic phases were combined, dried (MgSO$_4$) and the ether distilled through a 4 inch Vigreux column. The residue was then subjected to vacuum distillation to give 112 g (60% of theoretical) of the desired azide as a light yellow liquid having a boiling point (bp) of 44°-46° C. at 0.5 mm Hg.

The ketoesters employed as starting materials in the preparation of the present compounds are prepared by methods known in the art. One such method involves the general procedure of condensing an arylmethyl ketone with diethylcarbonate in the presence of potassium tertiary butoxide (t-BuO$^-$K$^+$). See, for example, J. March, *Advanced Organic Chemistry: Reaction, Mechanisms, and Structure*, p. 368, McGraw-Hill Book Co., New York, 1968, which is incorporated herein by reference.

EXAMPLE 8

Preparation of ethyl 4-fluoro-benzoylacetate

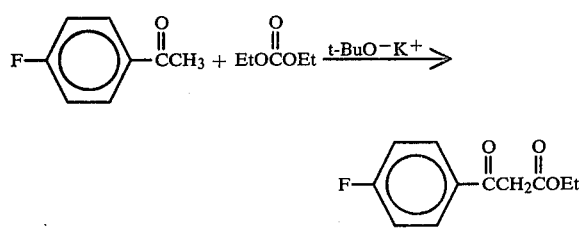

A mechanically stirred mixture of potassium tertiary butoxide (33.67 g, 0.3 mole), diethylcarbonate (200 ml) and 4-fluoroacetophenone (34.54 g, 0.25 mole) was heated at 90°-100° C. for 16 hours, cooled, poured into water (1200 ml), acidified with concentrated hydrochloric acid and extracted with ether (3×250 ml). The organic phases were combined, dried (MgSO$_4$) and the volatile material removed on a rotary evaporator. The dark oily residue was distilled to give 43.3 g (82%) of a light yellow liquid having a boiling point of 95°-100° C. at 0.3 mm Hg.

What is claimed is:

1. A compound of the formula

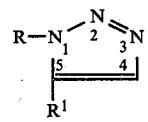

wherein
R represents

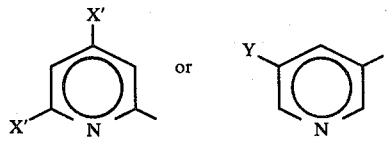

wherein
each X' independently represents CF$_3$, Cl, H or Br with the proviso that both of X' cannot be H;
Y represents CF$_3$, Cl or Br;
R$^1$ represents C$_1$-C$_8$ alkyl, C$_2$-C$_6$ alkenyl, C$_2$-C$_6$ alkynyl, C$_2$-C$_6$ alkoxyalkyl, CF$_3$ or Ar'';
Ar'' represents

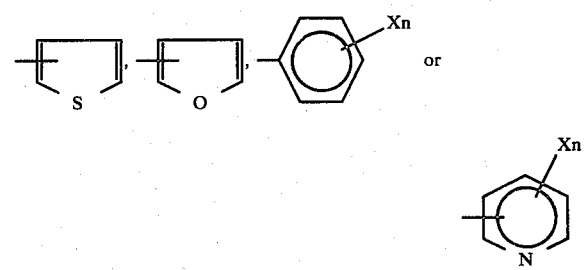

wherein
each X independently represents halo, C$_1$-C$_6$ alkyl, —OCH$_3$, —CF$_3$, —OCF$_3$, —NO$_2$, —CN or —CO$_2$R$^2$;
each n independently represents 0, 1 or 2; and
R$^2$ represents C$_1$-C$_6$ alkyl.

2. The compound of claim 1 which is 2-(5-phenyl-1H-1,2,3-triazol-1-yl)-4,6-bis(trifluoromethyl)pyridine.

3. The compound of claim 1 which is 2-(5-phenyl-1H-1,2,3-triazol-1-yl)-6-(trifluoromethyl)pyridine.

4. The compound of claim 1 which is 2-(5-phenyl-1H-1,2,3-triazol-1-yl)-6-chloropyridine; 2-(5-phenyl-1H-1,2,3-triazol-1-yl)-4,6-dichloropyridine; 2-(5-phenyl-1H-1,2,3-triazol-1-yl)-4-trifluoromethyl-6-chloropyridine; 2-(5-(4-fluoro)phenyl-1H-1,2,3-triazol-1-yl)-6-(trifluoromethyl)pyridine; 2-(5-(4-fluoro)phenyl-1H-1,2,3-triazol-1-yl)-4,6-bis(trifluoromethyl)pyridine; 2-(5-phenyl-1H-1,2,3-triazol-1-yl)-6-bromopyridine or 2-(5-phenyl-1H-1,2,3-triazol-1-yl)-4-chloro-6-(trifluoromethyl)pyridine.

5. The compound of claim 1 which is 2-(5-(4-fluoro)-phenyl-1H-1,2,3-triazol-1-yl)-6-(trifluoromethyl)pyridine.

6. The compound of claim 1 which is 2-(5-(4-fluoro)-phenyl-1H-1,2,3-triazol-1-yl)-4,6-bis(trifluoromethyl)-pyridine.

7. The compound of claim 1 which is 2-(5-phenyl-1H-1,2,3-triazol-1-yl)-6-bromopyridine.

8. A composition for the control of undesirable plant growth which comprises as an active agent one or more compounds of the following formula:

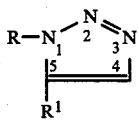

wherein
R represents

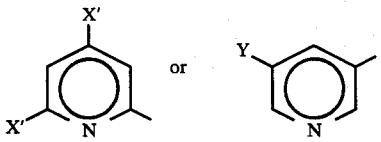

wherein
each X' independently represents $CF_3$, Cl, H or Br with the proviso that both of X' cannot be H;
Y represents $CF_3$, Cl or Br;
$R^1$ represents $C_1$–$C_8$ alkyl, $C_2$–$C_6$ alkenyl, $C_2$–$C_6$ alkynyl, $C_2$–$C_6$ alkoxyalkyl, —$CF_3$ or Ar'';
Ar'' represents

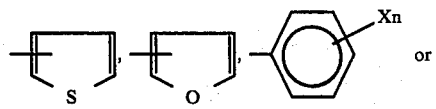 or 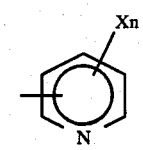

wherein
each X independently represents halo, $C_1$–$C_6$ alkyl, —$OCH_3$, —$CF_3$, —$OCF_3$, —$NO_2$, —CN or —$CO_2R^2$;
each n independently represents 0, 1 or 2; and
$R^2$ represents $C_1$–$C_6$ alkyl.

9. The composition of claim 8 wherein said active agent constitutes from about 0.001 to about 98 percent by weight of the total composition.

10. The composition of claim 8 wherein said active compound is 2-(5-phenyl-1H-1,2,3-triazol-1-yl)-4,6-bis(-trifluoromethyl)pyridine.

11. The composition of claim 8 wherein said active compound is 2-(5-phenyl-1H-1,2,3-triazol-1-yl)-6-(trifluoromethyl)pyridine.

12. The composition of claim 8 wherein said active compound is 2-(5-phenyl-1H-1,2,3-triazol-1-yl)-6-chloropyridine; 2-(5-phenyl-1H-1,2,3-triazol-1-yl)-4,6-dichloropyridine; 2-(5-phenyl-1H-1,2,3-triazol-1-yl)-4-trifluoromethyl-6-chloropyridine; 2-(5-(4-fluoro)phenyl-1H-1,2,3-triazol-1-yl)-6-(trifluoromethyl)pyridine; 2-(5-(4-fluoro)phenyl-1H-1,2,3-triazol-1-yl)-4,6-bis(tri-fluoromethyl)pyridine; 2-(5-phenyl-1H-1,2,3-triazol-1-yl)-4-chloro-6-(trifluoromethyl)pyridine; or 2-(5-phenyl-1H-1,2,3-triazol-1-yl)-6-bromopyridine.

13. The composition of claim 8 which is 2-(5-(4-fluoro)phenyl-1H-1,2,3-triazol-1-yl)-6-(trifluoromethyl)pyridine.

14. The composition of claim 8 which is 2-(5-(4-fluoro)phenyl-1H-1,2,3-triazol-1-yl)-4,6-bis(trifluoromethyl)pyridine.

15. The composition of claim 8 which is 2-(5-phenyl-1H-1,2,3-triazol-1-yl)-6-bromopyridine.

16. A method for inhibiting the growth of undesirable plant species which comprises applying to plants, plant parts or their habitats a growth-inhibiting amount of at least one active compound corresponding to the formula:

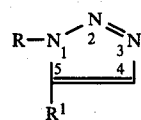

wherein
R represents

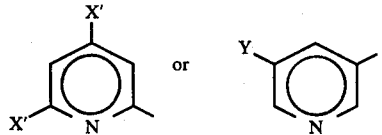

wherein
each X' independently represents $CF_3$, Cl, H or Br with the proviso that both of X' cannot be H;
Y represents $CF_3$, Cl or Br;
$R^1$ represents $C_1$–$C_8$ alkyl, $C_2$–$C_6$ alkenyl, $C_2$–$C_6$ alkynyl, $C_2$–$C_6$ alkoxyalkyl, $CF_3$ or Ar'';
Ar'' represents

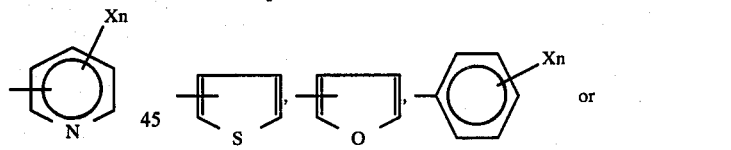 or

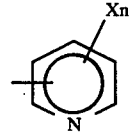

wherein
each X independently represents halo, $C_1$–$C_6$ alkyl, —$OCH_3$, —$CF_3$, —$OCF_3$, —$NO_2$, —CN or —$CO_2R^2$;
each n independently represents 0, 1 or 2; and
$R^2$ represents $C_1$–$C_6$ alkyl.

17. The method of claim 16 wherein said active compound is 2-(5-phenyl-1H-1,2,3-triazol-1-yl)-4,6-bis-(trifluoromethyl)pyridine.

18. The method of claim 16 wherein said active compound is 2-(5-phenyl-1H-1,2,3-triazol-1-yl)-6-(trifluoromethyl)pyridine.

19. The method of claim 16 wherein said active compound is 2-(5-phenyl-1H-1,2,3-triazol-1-yl)-6-chloropyridine; 2-(5-phenyl-1H-1,2,3-triazol-1-yl)-4,6- dichloropyridine; 2-(5-phenyl-1H-1,2,3-triazol-1-yl)-4-trifluoromethyl-6-chloropyridine; 2-(5-(4-fluoro)phenyl-1H-1,2,3-triazol-1-yl)-6-(trifluoromethyl)pyridine; 2-(5-(4-fluoro(phenyl-1H-1,2,3-triazol-1-yl)-4,6-bis(trifluoromethyl)pyridine; 2-(5-phenyl-1H-1,2,3-triazol-1-yl)-4-chloro-6-(trifluoromethyl)pyridine; or 2-(5-phenyl-1H-1,2,3-triazol-1-yl)-6-bromopyridine.

20. The method of claim 16 wherein said active compound is 2-(5-(4-fluoro)phenyl-1H-1,2,3-triazol-1-yl)-6-(trifluoromethyl)pyridine.

21. The method of claim 16 wherein said active compound is 2-(5-(4-fluoro)phenyl-1H-1,2,3-triazol-1-yl)-4,6-bis(trifluoromethyl)pyridine.

22. The method of claim 16 wherein said active compound is 2-(5-phenyl-1H-1,2,3-triazol-1-yl)-6-bromopyridine.

23. The method of claim 16 wherein said active compound is applied at a rate of from about 0.05 to about 10 pounds per acre.

24. The method of claim 16 wherein said active compound is applied at a rate of from about 0.1 to about 2 pounds per acre.

25. The method of claim 16 wherein said active compound is used to control undesirable annual grasses in cotton and soybean crops.

26. A compound of the formula

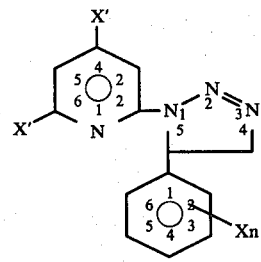

wherein
Each X independently represents halo, $C_1$–$C_6$ alkyl, —$OCH_3$, —$CF_3$, —$OCF_3$, —$NO_2$, —CN or $CO_2R^2$;
Each n independently represents 0, 1 or 2; and $R^2$ represents $C_1$–$C_6$ alkyl;
Each X' independently represents —$CF_3$ Cl, H, or Br with the proviso that both of the X' substituents cannot be H.

27. The compound of claim 26 wherein the pyridine ring has a halo or a —$CF_3$ group in the 4 or 6 pyridine ring position or both the 4 and 6 pyridine ring position.

28. The compound of claim 27 wherein the phenyl ring has a fluoro atom attached to the 4 phenyl ring position.

29. The compound of claim 27 wherein the pyridine ring carries a —$CF_3$ group attached to the 6 pyridine ring position.

30. The compound of claim 29 wherein the phenyl ring has a fluoro atom attached to the 4 phenyl ring position.

* * * * *